United States Patent
Yang et al.

(10) Patent No.: US 10,206,641 B2
(45) Date of Patent: *Feb. 19, 2019

(54) RADIOGRAPHY SYSTEM AND MOVING METHOD THEREOF

(71) Applicant: Samsung Electronics Co., Ltd., Suwon-si (KR)

(72) Inventors: Soo Sang Yang, Suwon-si (KR); Woo Sup Han, Yongin-si (KR); Hyun Woong Hwang, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/620,147

(22) Filed: Jun. 12, 2017

(65) Prior Publication Data

US 2017/0273648 A1 Sep. 28, 2017

Related U.S. Application Data

(63) Continuation of application No. 14/150,760, filed on Jan. 8, 2014, now Pat. No. 9,675,308, which is a
(Continued)

(30) Foreign Application Priority Data

Oct. 6, 2010 (KR) ........................ 10-2010-0097304

(51) Int. Cl.
    *A61B 6/00* (2006.01)
    *A61B 6/04* (2006.01)

(52) U.S. Cl.
    CPC .......... *A61B 6/4476* (2013.01); *A61B 6/4405* (2013.01); *A61B 6/4452* (2013.01);
(Continued)

(58) Field of Classification Search
    CPC ........................... A61B 6/4405; A61B 6/4482
    See application file for complete search history.

(56) References Cited

U.S. PATENT DOCUMENTS 4,107,590 A    8/1978   Pury et al.
4,163,929 A    8/1979   Janu et al.
(Continued)

FOREIGN PATENT DOCUMENTS

CN    1334772 A    2/2002
CN    1929785 A    3/2007
(Continued)

OTHER PUBLICATIONS

European Search Report dated Dec. 13, 2017 in corresponding European Patent Application No. 15786291.3 (12 pages in English).
(Continued)

*Primary Examiner* — Thomas R Artman
(74) *Attorney, Agent, or Firm* — NSIP Law

(57) ABSTRACT

A radiography system is provided. The radiography system includes a radiographic device arranged in a movable manner, a measuring device to measure at least one of external force and torque applied to the radiographic device, and a drive device to move the radiographic device based on a direction and magnitude of the at least one of the force and torque measured by the measuring device.

21 Claims, 8 Drawing Sheets

Related U.S. Application Data continuation of application No. 13/237,219, filed on Sep. 20, 2011, now Pat. No. 8,651,740.

(52) U.S. Cl.
CPC .......... *A61B 6/4464* (2013.01); *A61B 6/4482* (2013.01); *A61B 6/547* (2013.01); *A61B 6/0407* (2013.01); *A61B 6/467* (2013.01); *A61B 6/587* (2013.01)

(56) References Cited

U.S. PATENT DOCUMENTS

| | | | |
|---|---|---|---|
| 4,674,107 | A | 6/1987 | Urban et al. |
| 4,697,661 | A | 10/1987 | Pajerski et al. |
| 4,926,455 | A | 5/1990 | Stojkov et al. |
| 5,351,282 | A | 9/1994 | Kadowaki et al. |
| 5,416,819 | A | 5/1995 | Uzuyama et al. |
| 5,572,567 | A | 11/1996 | Khutoryansky et al. |
| 5,768,336 | A | 6/1998 | Khutoryansky et al. |
| 6,422,747 | B2 | 7/2002 | Akutsu et al. |
| 6,851,851 | B2 | 2/2005 | Smith et al. |
| 6,871,715 | B1 | 3/2005 | Díaz Carmena et al. |
| 7,177,393 | B2 | 2/2007 | Kanemitsu |
| 7,329,046 | B1 | 2/2008 | Muszak et al. |
| 7,534,037 | B2 | 5/2009 | Curtis |
| 7,597,473 | B2 | 10/2009 | Graumann et al. |
| 7,809,102 | B2 | 10/2010 | Brada et al. |
| 8,201,999 | B2 | 6/2012 | Uchida et al. |
| 8,419,276 | B2 | 4/2013 | Oda et al. |
| 8,553,842 | B2 | 10/2013 | Moon et al. |
| 8,651,740 | B2 * | 2/2014 | Yang ............... A61B 6/4452 378/196 |
| 8,755,492 | B2 * | 6/2014 | Lee ............... H05G 1/02 378/115 |
| 8,848,865 | B2 | 9/2014 | Nakayama |
| 9,149,247 | B2 | 10/2015 | Lee et al. |
| 9,532,763 | B2 | 1/2017 | Lee et al. |
| 9,675,308 | B2 * | 6/2017 | Yang ............... A61B 6/4452 |
| 9,687,205 | B2 * | 6/2017 | Lee ............... A61B 6/4452 |
| 9,757,080 | B2 | 9/2017 | Lee et al. |
| 2002/0080921 | A1 | 6/2002 | Smith et al. |
| 2006/0120512 | A1 | 6/2006 | Watanabe |
| 2006/0126795 | A1 | 6/2006 | Lumma |
| 2007/0112458 | A1 | 5/2007 | Kondo et al. |
| 2008/0025469 | A1 | 1/2008 | Watanabe |
| 2009/0285355 | A1 | 11/2009 | Brada et al. |
| 2010/0215152 | A1 | 8/2010 | Takahashi |
| 2010/0243924 | A1 | 9/2010 | Uchida et al. |
| 2010/0329426 | A1 | 12/2010 | Oda et al. |
| 2012/0087479 | A1 | 4/2012 | Moon et al. |
| 2012/0087480 | A1 | 4/2012 | Yang et al. |
| 2012/0155616 | A1 | 6/2012 | Rijken et al. |
| 2012/0277625 | A1 | 11/2012 | Nakayama |
| 2013/0121477 | A1 | 5/2013 | Lee et al. |
| 2013/0343523 | A1 | 12/2013 | Lee et al. |
| 2014/0119516 | A1 | 5/2014 | Yang et al. |
| 2014/0321621 | A1 | 10/2014 | Lee et al. |
| 2014/0328456 | A1 | 11/2014 | Lee et al. |
| 2015/0012168 | A1 | 1/2015 | Kuklish et al. |
| 2015/0043716 | A1 | 2/2015 | Lee et al. |
| 2015/0313561 | A1 | 11/2015 | Kwak |
| 2015/0351711 | A1 | 12/2015 | Lee et al. |
| 2016/0220215 | A1 | 8/2016 | Kwak et al. |

FOREIGN PATENT DOCUMENTS

| | | |
|---|---|---|
| CN | 102551747 A | 7/2012 |
| CN | 102949196 A | 3/2013 |
| EP | 1 642 693 A1 | 4/2006 |
| JP | 9-220220 A | 8/1997 |
| JP | 11-324 A | 1/1999 |
| JP | 2003-81598 A | 3/2003 |
| JP | 2005-237613 A | 9/2005 |
| JP | 2010-227290 A | 10/2010 |
| JP | 2011-30699 A | 2/2011 |
| KR | 10-2012-0036562 A | 4/2012 |
| WO | WO 2009/136452 A1 | 11/2009 |
| WO | WO 2011/030255 A1 | 3/2011 |

OTHER PUBLICATIONS

U.S. Office Action dated Oct. 12, 2017, in corresponding U.S. Appl. No. 14/523,571

Korean Office Action dated Jun. 24, 2013, in counterpart Korean Application No. 10-2010-0097304 (16 pages, including complete English translation translated by Google Translate).

Chinese Office Action dated Apr. 3, 2014, in counterpart Chinese Application No. 201110302134.5 (8 pages, in Chinese, no English translation).

Chinese Office Action dated Nov. 27, 2014, in counterpart Chinese Application No. 201110302134.5 (25 pages, in Chinese, including complete English translation).

International Search Report dated Jul. 27, 2015, in counterpart International Application No. PCT/KR2015/004018 (3 pages, in English).

Chinese Notice of Allowance dated Aug. 6, 2015, in counterpart Chinese Application No. 201110302134.5 (4 pages, in Chinese, including complete English translation).

Korean Notice of Allowance dated Jun. 28, 2016, in counterpart Korean Application No. 10-2010-0097304 (7 pages, in Korean, including partial English translation).

Chinese Office Action dated Jan. 19, 2017, in counterpart Chinese Application No. 201510252782.2 (13 pages, in Chinese, including complete English translation).

U.S. Appl. No. 14/150,760, filed Jan. 8, 2014, Soo Sang Yang et al.
U.S. Appl. No. 14/264,500, filed Apr. 29, 2014, Dong Jae Lee et al.
U.S. Appl. No. 14/279,859, filed May 16, 2014, Dong Jae Lee et al.
U.S. Appl. No. 14/523,571, filed Oct. 24, 2014, Dong Jae Lee et al.

Chinese Office Action dated Sep. 12, 2017 in corresponding Chinese Patent Application No. 201510252782.2 (14 pages in English and 10 pages in Chinese).

Chinese Office Action dated Apr. 10, 2018 in corresponding Chinese Patent Application No. 201510252782.2 (22 pages in English and 16 pages in Chinese).

Extended European Search Report dated May 18, 2018 in corresponding European Patent Application No. 15786291.3 (12 pages in English).

Chinese Office Action dated Oct. 24, 2018, in corresponding Chinese Application No. 201510252782.2 (6 pages in English, 4 pages in Chinese).

* cited by examiner

RADIOGRAPHY SYSTEM AND MOVING METHOD THEREOF

CROSS-REFERENCE TO RELATED APPLICATIONS

This application is a continuation of application Ser. No. 14/150,760 filed on Jan. 8, 2014, now U.S. Pat. No. 9,675,308 issued on Jun. 13, 2017, which is a continuation of application Ser. No. 13/237,219 filed on Sep. 20, 2011, now U.S. Pat. No. 8,651,740 issued on Feb. 18, 2014, and claims the benefit of Korean Patent Application No. 10-2010-0097304 filed on Oct. 6, 2010, in the Korean Intellectual Property Office, the entire disclosures of which are incorporated herein by reference for all purposes.

BACKGROUND

1. Field

The following description relates to a radiography system and a moving method thereof.

2. Description of Related Art

A radiography system is widely used to process an images of an interior images of the human body using x-rays and is used in examination of internal injuries to the human body or diseases affecting the human body that are difficult to detect based on externally looking at the human body. To obtain an interior image of a selected region of the human body, such as the head or the chest, the radiography system transmits x-rays to the selected region and detects the transmitted x-rays.

The radiography system includes an x-ray tube to transmit x-rays to the region. The x-ray tube is movable to inspect various regions of the body.

A conventional ceiling type radiography system includes at least one guide rail mounted to the ceiling of an inspection room and a telescopic post frame extending up and down connected to the guide rail. The x-ray tube is rotatably connected to a lower end of the telescopic post frame.

Recently, an automated movement mode has been developed in which an actuator is connected to a moving shaft of the ceiling type radiography system and automatically moves the x-ray tube to a desired position input by a user.

The radiography system may also include a manual movement mode to allow the user to manually move the x-ray tube. A manual operating switch may be provided on the x-ray tube to activate the manual movement mode. The user may manually move the x-ray tube after switching from the automated movement mode to the manual movement mode using the manual operating switch.

Moving the x-ray tube, when in the manual movement mode, may require the user to apply a great force or torque to the x-ray tube due to 1) the weight of the x-ray tube and 2) friction resistance at each drive shaft of the radiography system. Therefore, repeatedly moving the x-ray tube, in the manual movement mode, may cause the user to get tired and physically fatigued.

SUMMARY

In one general aspect, there is provided a radiography system includes a radiographic device arranged in a movable manner, a measuring device to measure at least one of external force and torque applied to the radiographic device, and a drive device to move the radiographic device based on a direction and magnitude of the at least one of the force and torque measured by the measuring device.

The radiography system may further include a first guide rail fixed to a ceiling extending in a first direction, the radiographic device may be movable in the first direction along the first guide rail, the measuring device may include a first force sensor to measure external force applied to the radiographic device in the first direction, and the drive device may include a first drive device to move the radiographic device in the first direction.

The radiography system may further include a second guide rail slidably coupled to the first guide rail, the second guide rail extending in a second direction perpendicular to the first direction, the radiographic device may be movable in the second direction along the second guide rail, the measuring device may further include a second force sensor to measure external force applied to the radiographic device in the second direction, and the drive device may further include a second drive device to move the radiographic device in the second direction.

The radiography system may further include a post frame having a length of which increases or decreases in a third direction perpendicular to the first direction and the second direction, the radiographic device may be movable in the third direction as the length of the post frame increases or decreases, the measuring device may further include a third force sensor to measure external force applied to the radiographic device in the third direction, and the drive device may further include a third drive device to move the radiographic device in the third direction.

The third force sensor may be arranged near an output of the third drive device.

The radiography system may further include a first rotating joint rotatable in a fourth direction, the fourth direction being defined as a rotating direction about an axis substantially parallel to the third direction, the radiographic device may be connected to the first rotating joint and is rotatable in the fourth direction, the measuring device may further include a first torque sensor to measure torque applied to the radiographic device in the fourth direction, and the drive device may further include a fourth drive device to rotate the radiographic device in the fourth direction.

The radiography system may further include a second rotating joint rotatable in a fifth direction, the fifth direction being defined as a rotating direction about an axis substantially parallel to the first direction, the radiographic device may be connected to the second rotating joint and is rotatable in the fifth direction, the measuring device may further include a second torque sensor to measure torque applied to the radiographic device in the fifth direction, and the drive device may further include a fifth drive device to rotate the radiographic device in the fifth direction.

The radiography system may further include a control device connected to both the measuring device and the drive device.

The control device may control the magnitude and direction of drive force of the drive device based on a value measured by the measuring device.

The measuring device may include a force torque sensor to measure force applied along each of three axes perpendicular to one another and torque applied along each of at least two of the three axes.

The radiography system may further include a handle fixed to a side surface of the radiographic device so as to apply at least one of force and torque to the radiographic device, the force torque sensor may be arranged between the handle and the radiographic device.

The radiography system may further include a rotating joint connected to the radiographic device to enable rotation of the radiographic device, the force torque sensor may be arranged between the radiographic device and the rotating joint.

A single force sensor may include the first, second, and third force sensors.

In another aspect, there is provided a moving method of a radiography system including a radiographic device to transmit X-rays, a measuring device to measure at least one of force and torque applied to the radiographic device, and a drive device connected to the radiographic device to move the radiographic device, include applying at least one of force and torque to the radiographic device to move the radiographic device, measuring at least one of the force and torque applied to the radiographic device using the measuring device, and moving the radiographic device based on the direction and magnitude of at least one of the measured force and torque using the drive device.

The radiography system may further include a control device connected to both the measuring device and the drive device, and the moving method may further include controlling operation of the drive device using the control device by determining the direction and magnitude of drive force of the drive device based on the direction and magnitude of at least one of the measured force and torque.

The radiography method may further include periodically monitoring the direction and magnitude of at least one of the measured force and torque using the control device.

The radiography system may further include a handle fixed to the radiographic device for user grip, and the measuring device and the drive device may be operated only when the user grips the handle.

In still another aspect, there is provided a moving method of a radiography system including a radiographic device to transmit X-rays and a drive device connected to the radiographic device to move the radiographic device, includes measuring a first current value of the drive device when no external force and torque is applied to the radiographic device, measuring a second current value of the drive device when at least one of external force and torque is applied to the radiographic device, determining the direction and magnitude of at least one of the external force and torque applied to the radiographic device via a difference between the first current value and the second current value, and moving the radiographic device by operating the drive device based on the determined direction and magnitude of at least one of the force and torque.

In still another aspect, there is provided a radiography system including a radiographic device capable of being moved in at least one first direction, a controller capable of receiving an external force and torque in at least one second direction, a measuring device capable of measuring the received external force and torque in the at least one second direction, a translating device configured to translate the received external force and torque received by the controller in the at least one second direction to be applied to the radiographic device in a first direction, and a drive device to move the radiographic device in the at least one first direction based on the translated measured received external force and torque in the at least one second direction.

The at least one first direction may be in the same direction as the at least one second direction.

Other features and aspects may be apparent from the following detailed description, the drawings, and the claims.

Figure 1:
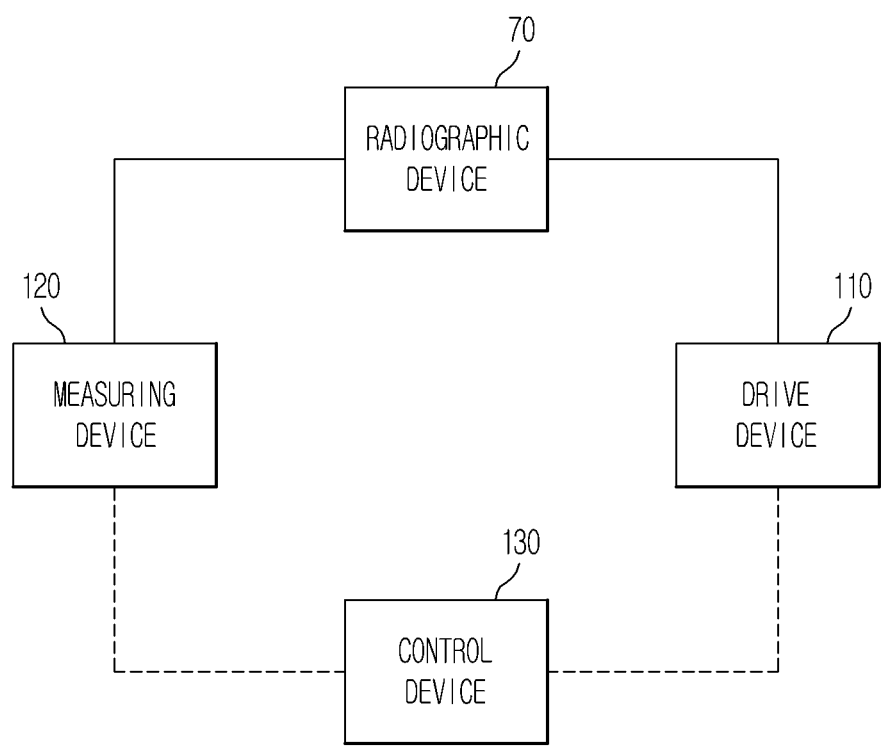
FIG. 1 is a conceptual view illustrating structures of a radiography system, according to an example embodiment.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the systems, apparatuses and/or methods described herein will be suggested to those of ordinary skill in the art. Also, descriptions of well-known functions and constructions may be omitted for increased clarity and conciseness.

FIG. 1 through FIG. 4 illustrate examples of a structure of radiography system.

Referring to FIG. 1, a radiographic device 70 may be mechanically coupled to a measuring device 120 and a drive device 110. A control device 130 may be connected to the measuring device 120 and the drive device 110 electrically. Each device will be described later in detail.

Figure 2:
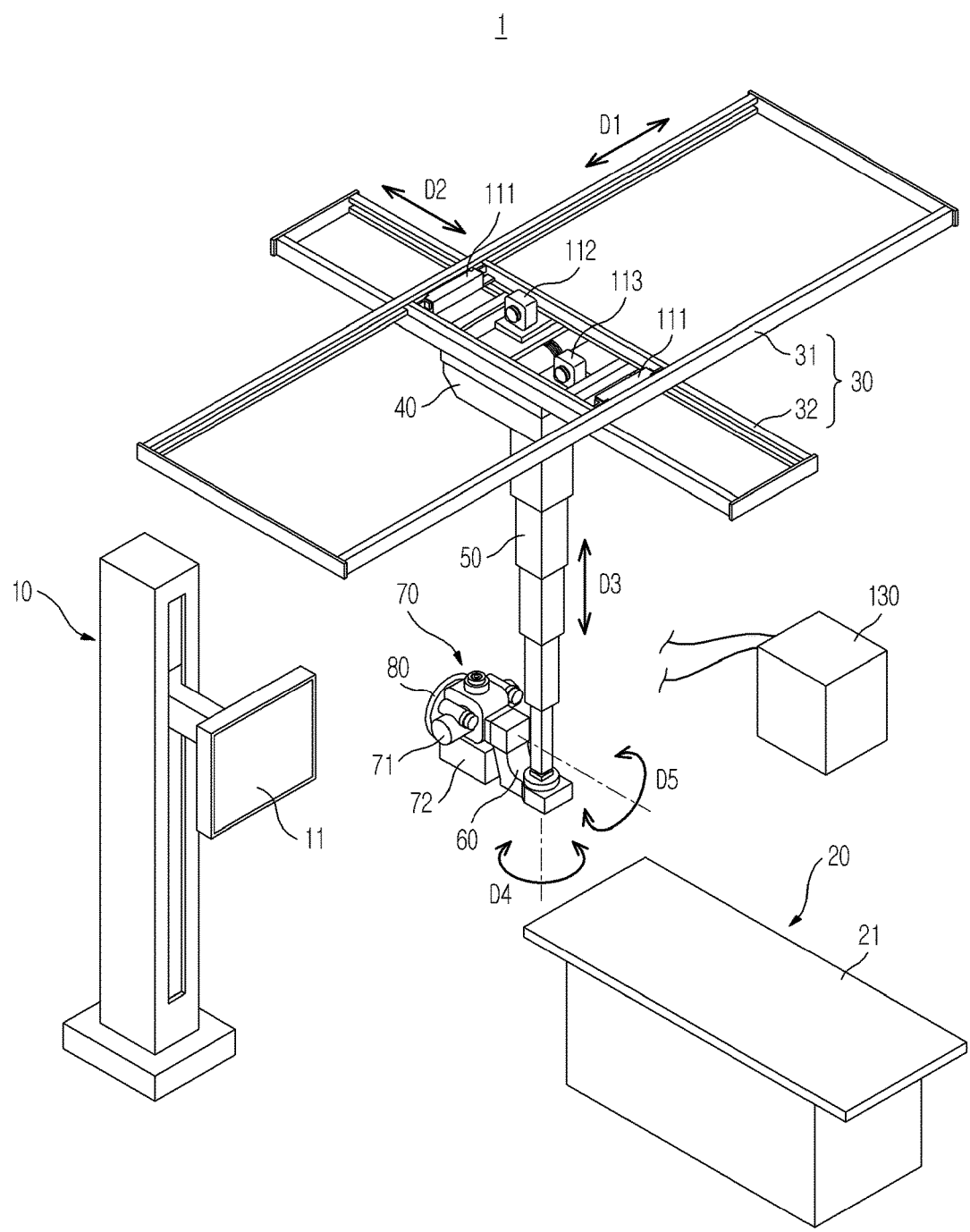
FIG. 2 is a perspective view of the radiography system, according to an example embodiment.

Referring to FIGS. 2 through to 4, the radiography system 1 may include a guide rail 30, a moving carriage 40, a post frame 50, the radiographic device 70, and the drive device 110. The radiography system 1 may further include a stand 10 and a table 20, which include respective x-ray receivers 11 and 21.

The guide rail 30, moving carriage 40, and post frame 50 may aid in moving the radiographic device 70 to the desired location.

The guide rail 30 may include a first guide rail 31 and a second guide rail 32 which are oriented at an angle with respect to each other and have a predetermined angle therebetween. The first guide rail 31 and the second guide rail 32 may extend perpendicularly with respect to each other.

The first guide rail 31 may be mounted to the ceiling of an inspection room in which the radiography system 1 is located. The second guide rail 32 may be located beneath the first guide rail 31 and may be slidably installed to the first guide rail 31. The first guide rail 31 may have a roller (not shown) which moves along a length or a longitudinal axis of the first guide rail 31. The second guide rail 32 may also be connected to the roller (not shown) which moves along the length or the longitudinal axis of the first guide rail 31.

A direction of extension of the first guide rail 31 may be referred to as a first direction D1 and a direction of extension of the second guide rail 32 may be referred to as a second direction D2. The first direction D1 and the second direction D2 may be perpendicular to each other and may be parallel to the ceiling of the inspection room.

The moving carriage 40 may be located beneath the second guide rail 32 and is movable on the second guide rail 32. The moving carriage 40 may be provided with a roller (not shown) which is movable along a length or a longitudinal axis of the second guide rail 32. In other words, the moving carriage 40 may be movable in the first direction D1 along with the second guide rail 32, and also be movable along the second guide rail 32 in the second direction D2.

The post frame 50 may be secured to the moving carriage 40 and may be located underneath the moving carriage 40. The post frame 50 may be made up of a plurality of posts.

The plurality of posts may be connected to one another in a telescopic manner so that the post frame 50 a variable vertical length that can be adjusted vertically. A direction in which the post frame 50 may be variable in length is referred to as a third direction D3. Thus, the third direction D3 may be perpendicular to both the first direction D1 and the second direction D2.

The radiographic device 70 may transmit x-rays to a subject to be x-rayed. The radiographic device 70 may be an x-ray tube. The x-ray tube may include an x-ray source 71 to generate x-rays and a collimator 72 to guide the generated x-rays toward the subject.

A rotating joint 60 may be provided between the radiographic device 70 and the post frame 50. The rotating joint 60 couples the radiographic device 70 to the post frame 50 and supports a load applied to the radiographic device 70.

The rotating joint 60 may include a first rotating joint 61 connected to a lower end of the post frame 50 and a second rotating joint 62 connected to the radiographic device 70.

The first rotating joint 61 may be rotatable about a center axis of the post frame 50 vertically extending in the inspection room. Accordingly, the first rotating joint 61 may be rotatable in a plane perpendicular to the third direction D3. A rotating direction of the first rotating joint 61 may be referred to as a fourth direction D4. The fourth direction D4 may be a rotating direction about an axis parallel to the third direction D3.

The second rotating joint 62 may be rotatable in a plane perpendicular to the ceiling of the inspection room. Thus, the second rotating joint 62 may be rotatable about an axis parallel to the first direction D1 or the second direction D2. A rotating direction of the second rotating joint 62 may be referred to as a fifth direction D5. The fifth direction D5 may be a rotating direction about an axis extending in the first direction D1 or the second direction D2.

The radiographic device 70 may be connected to the rotating joint 60 and is rotatable in the fourth direction D4 and the fifth direction D5. Additionally, the radiographic device 70 may be connected to the post frame 50 via the rotating joint 60 and may be linearly movable in the first direction D1, the second direction D2 and third direction D3.

The drive device 110 may move the radiographic device 70 in the first to fifth directions D1 to D5. The drive device 110 may be an electrically driven motor. The drive device 110 may include first, second, third, fourth and fifth drive devices 111, 112, 113, 114 and 115 corresponding to the first to fifth directions D1 to D5 respectively.

The drive devices 111, 112, 113, 114 and 115 may be arranged at various positions for convenience of design. For example, the first drive device 111 may serve to move the second guide rail 32 in the first direction D1 and may be located near the first guide rail 31. The second drive device 112 may serve to move the moving carriage 40 in the second direction D2 and may be located near the second guide rail 32. The third drive device 113 may serve to increase or decrease the length of the post frame 50 in the third direction D3 and may be located in the moving carriage 40. In addition, the fourth drive device 114 may serve to rotate the radiographic device 70 in the fourth direction D4 and may be located near the first rotating joint 61. The fifth drive device 115 may serve to rotate the radiographic device 70 in the fifth direction D5 and may be located near the second rotating joint 62.

Each drive device 110 may be connected to a power transmission mechanism (not shown) to enable linear movement or rotation of the radiographic device 70 in the first to fifth directions D1 to D5. The power transmission mechanism (not shown) may generally include belts and pulleys, chains and sprockets, shafts, etc.

A moving handle 80 for a user to grip may be provided near the radiographic device 70. The moving handle 80 may be secured to the radiographic device 70 to allow the user to move the radiographic device 70 by applying force or torque. Movement of the radiographic device 70 will be described hereinafter.

An operating panel 90 may be provided for inputting a variety of radiography information and to operate the aforementioned devices. The operating panel 90 is located at a position assuring easy access and manipulation by the user and may be located at a surface of the radiographic device 70.

The control device 130 may be connected to the respective devices of the radiography system 1 including the drive device 110 and the operating panel 90 to control the respective devices.

The control device 130 may be connected to the drive device 110 and may be configured to move the radiographic device 70 to a desired position. For example, if the user inputs a desired radiography position to the operating panel 90, the control device 130 judges a current position and the inputted desired radiography position, and controls operation of the drive device 110 required to be driven. With operation of the drive device 110, the radiographic device 70 may be moved to the desired radiography position inputted by the user. This mode may be referred to as the automated movement mode.

On the other hand, the user may directly move the radiographic device 70 by applying force or torque. This mode may be referred to as the manual movement mode. A mode converter 81 may be provided to switch the mode from the automated movement mode to the manual movement mode. The mode converter 81 may be a switch integrated with the operating panel 90, or a switch may be provided on the moving handle 80. If the mode converter 81 is integrated with the moving handle 80, the manual movement mode may be activated when the user grips the moving handle 80, and may be switched to the automated movement mode when the user releases the moving handle 80.

To move the radiographic device 70 in the manual movement mode, a large force or torque may be necessary to overcome friction to move each drive device 110. Therefore, operating the drive device 110 based on the user's desired movement may allow the radiographic device 70 to be moved even with a force or torque less than the necessary large force or torque. Here, the user's desired movement may be determined based on the force or torque applied to the radiographic device 70 by the user. The manual movement mode in which the drive device 110 operates based on the user's desired movement to move the radiographic device 70 may be referred to as a power-assisted movement mode to avoid confusion with a manual movement mode in which the user manually moves a radiographic device without a drive device operating.

Thus, to determine the user's desired movement, the radiography system 1 may include the measuring device 120 to measure force or torque applied by the user.

The measuring device 120 may be connected to the control device 130 to allow the control device 130 to operate the drive device 110 based on the force or torque measured by the measuring device 120.

The measuring device 120 may include 1) first, second and third force sensors 121, 122 and 123 to measure a force applied in the first, second and third directions D1, D2 and D3, and 2) first and second torque sensors 124 and 125 to measure torque applied in the fourth and fifth directions D4 and D5.

Figure 3:
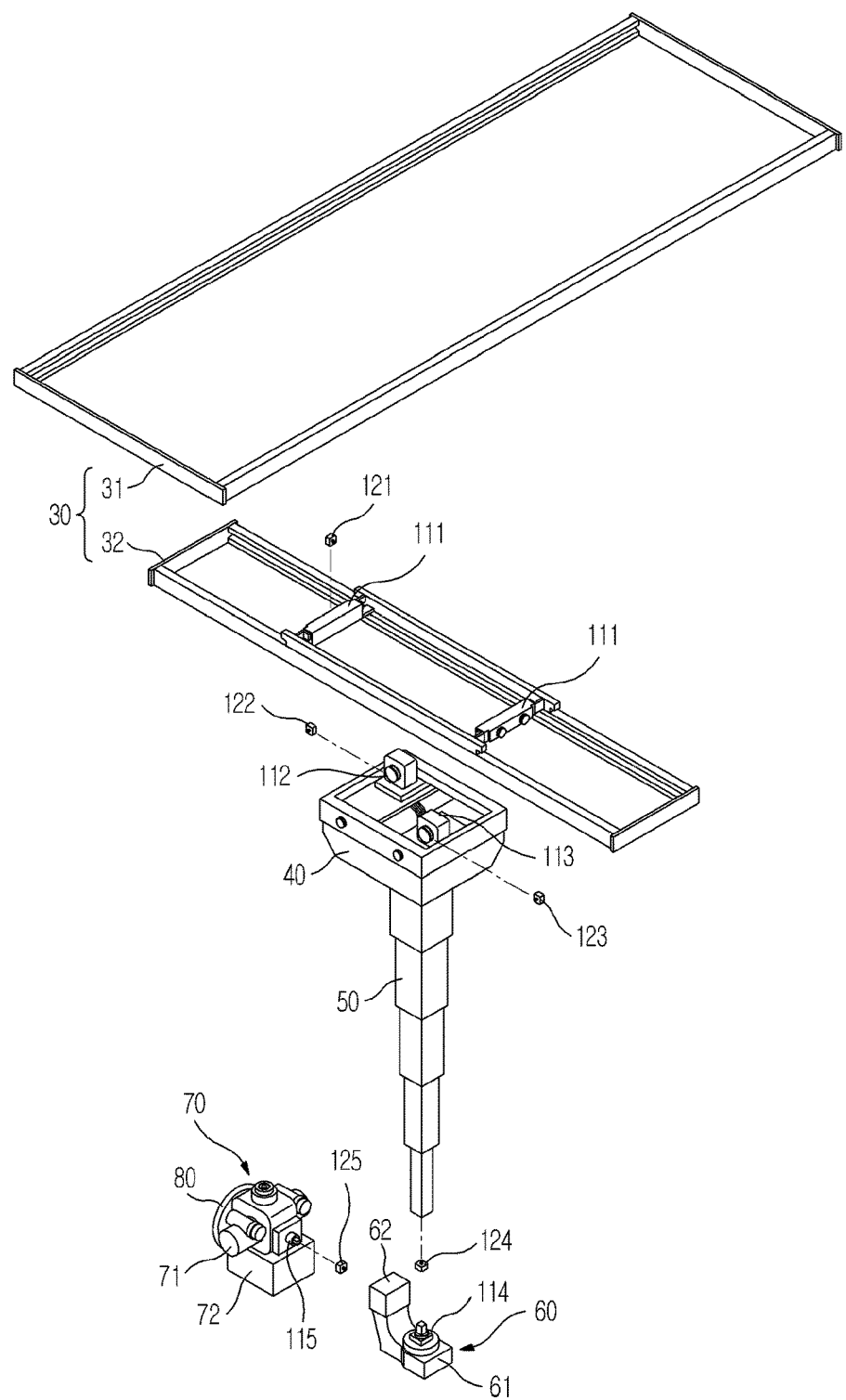
FIG. 3 is an exploded perspective view of the radiography system, according to an example embodiment.
Figure 4:
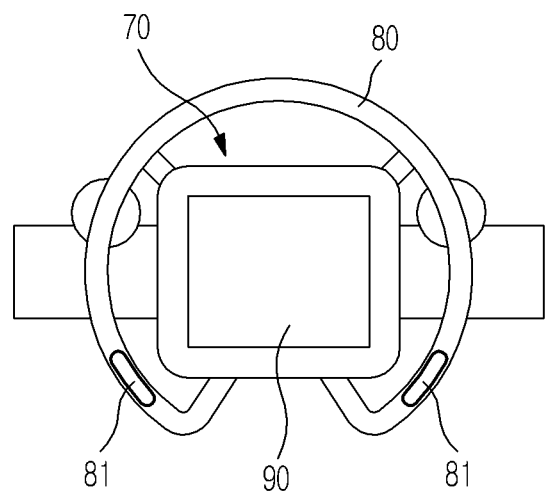
FIG. 4 is a side view illustrating a moving handle provided in the radiography system, according to an example embodiment.

The first force sensor 121 may serve to measure a direction and magnitude of force in the first direction D1. The first force sensor 121 may be located at a position to which the force in the first direction D1 is measurable. As illustrated in FIG. 3, the first force sensor 121 may be located near the first drive device 111. Since the force applied by the user in the first direction D1 may be transmitted to an output end of the first drive device 111, the first force sensor 121 connected to the output end of the first drive device 111 may measure the direction and magnitude of the force in the first direction D1.

The position of the first force sensor 121 is not limited to near the first drive device 111 and may be located anywhere so long as it may measure the force in the first direction D1. For example, the first force sensor 121 may be disposed between the radiographic device 70 and the rotating joint 60, or between the rotating joint 60 and the lower end post of the post frame 50. Note that positioning the first force sensor 121 between the radiographic device 70 and the rotating joint 60 may make it impossible for the first force sensor 121 to measure the force in the first direction D1 directly applied to the post frame 50 without passing through the radiographic device 70. In this case, accordingly, it may be necessary for the user to apply force to the moving handle 80 or the radiographic device 70 in the first direction D1 in order to move the radiographic device 70 in the first direction D1.

Similarly, the second force sensor 122 and the third force sensor 123 may be arranged at arbitrary positions to measure a force in the second direction D2 and a force in the third direction D3, respectively. As illustrated in FIG. 3, the second force sensor 122 may be located near an output end of the second drive device 112, and the third force sensor 123 may be located near an output end of the third drive device 113.

The first torque sensor 124 may serve to measure a direction and magnitude of torque in the fourth direction D4. If the user applies torque in the fourth direction D4 to rotate the radiographic device 70 in the first direction D4, the first torque sensor 124 may measure the direction and magnitude of the torque. As such, the first torque sensor 124 is located to allow measurement of the torque in the fourth direction D4. As illustrated in FIG. 3, the first torque sensor 124 may be located between the lower end post of the post frame 50 and the first rotating joint 61 and may be connected to both the lower end post of the post frame 50 and the first rotating joint 61.

The second torque sensor 125 may be located at an arbitrary position to measure torque in the fifth direction D5. As illustrated in FIG. 3, the second torque sensor 125 may be disposed between the second rotating joint 62 and the radiographic device 70.

Although the first, second and third force sensors 121, 122 and 123 and the first and second torque sensors 124 and 125 have been described as being provided to measure force or torque in each direction, two or more sensors may be integrated with one another. For example, the first, second and third force sensors 121, 122 and 123 may be replaced by a force sensor designed to measure forces in three directions perpendicular to one another, and the first and second torque sensors 124 and 125 may be replaced by a torque sensor designed to measure torque in two directions. Additionally, the measuring device 120 may take the form of various combinations of these force sensors and torque sensors based on characteristics thereof.

Figure 5A:
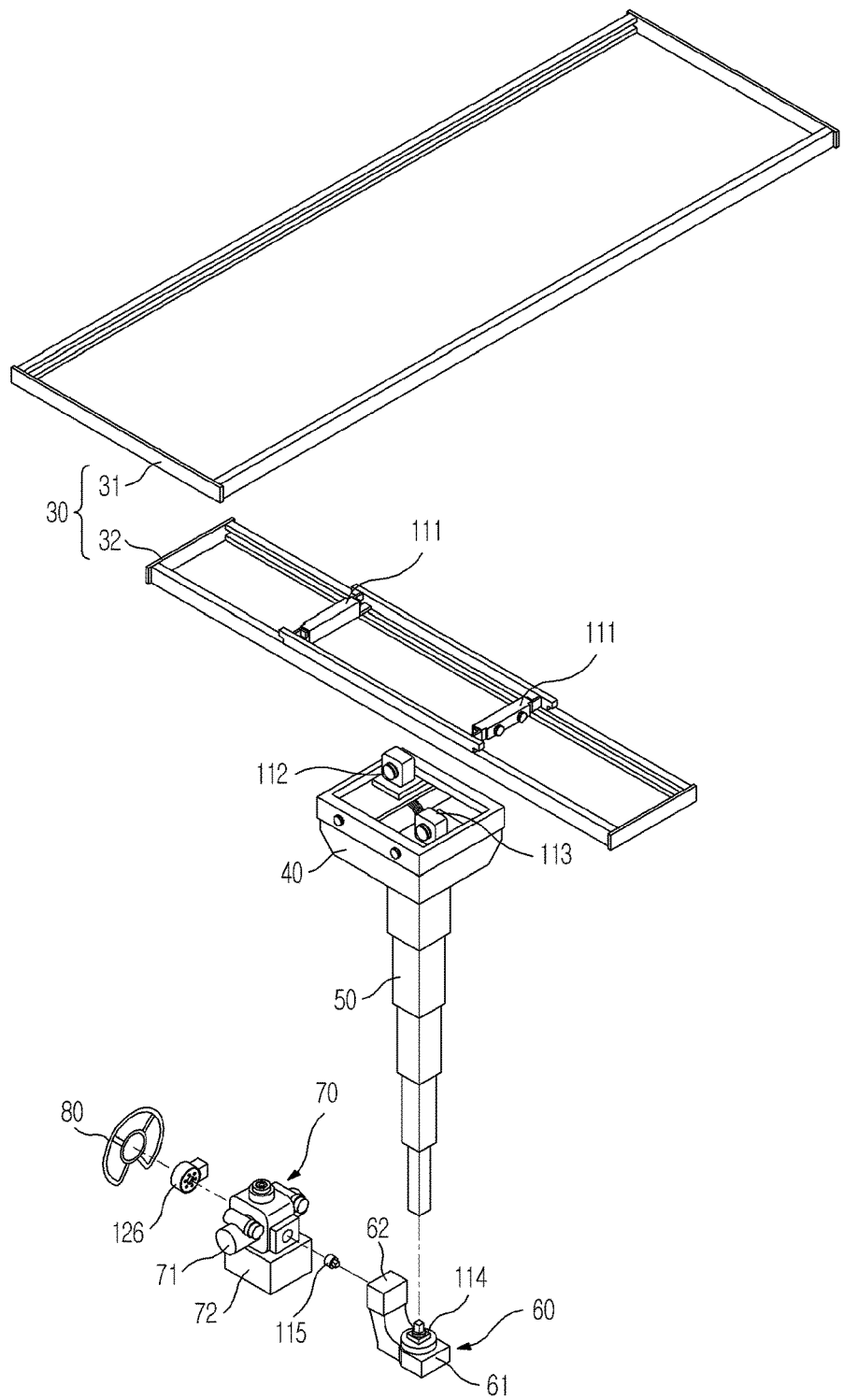
FIG. 5A is an exploded perspective view of a radiography system, according to another example embodiment.
Figure 5B:
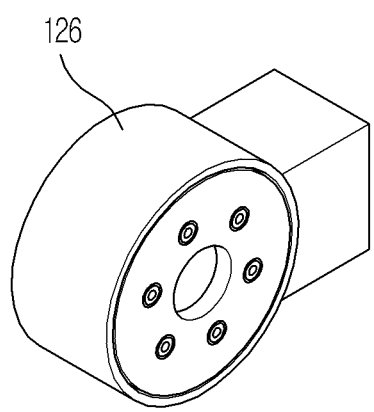
FIG. 5B is a perspective view of a force torque sensor provided in the radiography system of FIG. 5A.

FIG. 5A illustrates an exploded perspective view of a radiography system, and FIG. 5B illustrates a perspective view of a force torque sensor provided in the radiography system of FIG. 5A.

Referring to FIGS. 5A and 5B, the measuring device 120 may include a force torque sensor 126.

The force torque sensor 126 may measure forces in three directions perpendicular to one another and rotational torque with respect to each of the three directions. As such, the force torque sensor 126 may have an ability to measure force and torque along a total of six axes, and therefore may function to measure the three directional forces applied in the first to third directions D1 to D3 and the two directional torques applied in the fourth and fifth directions D4 and D5.

The force torque sensor 126 may be connected to the control device 130 to transmit the measured direction and magnitude of force or torque to the control device 130.

The force torque sensor 126 may be located near the radiographic device 70 to understand the user's desired movement by measuring the force or torque applied to the radiographic device 70. To this end, the force torque sensor 126 may be located between the moving handle 80 and the radiographic device 70. Since the user grips the moving handle 80 to apply force or torque to the moving handle 80 when in the manual movement mode, connecting the force torque sensor 126 to the moving handle 80 enables an accurate measurement of the force or torque.

The force torque sensor 126 may be provided between the radiographic device 70 and the rotating joint 60 and may be connected both to the radiographic device 70 and the rotating joint 60. Even if the user directly applies force or torque to the radiographic device 70 by a means other than the moving handle 80, positioning the force torque sensor 126 at the above-described position enables measurement of the force or torque.

Figure 6:
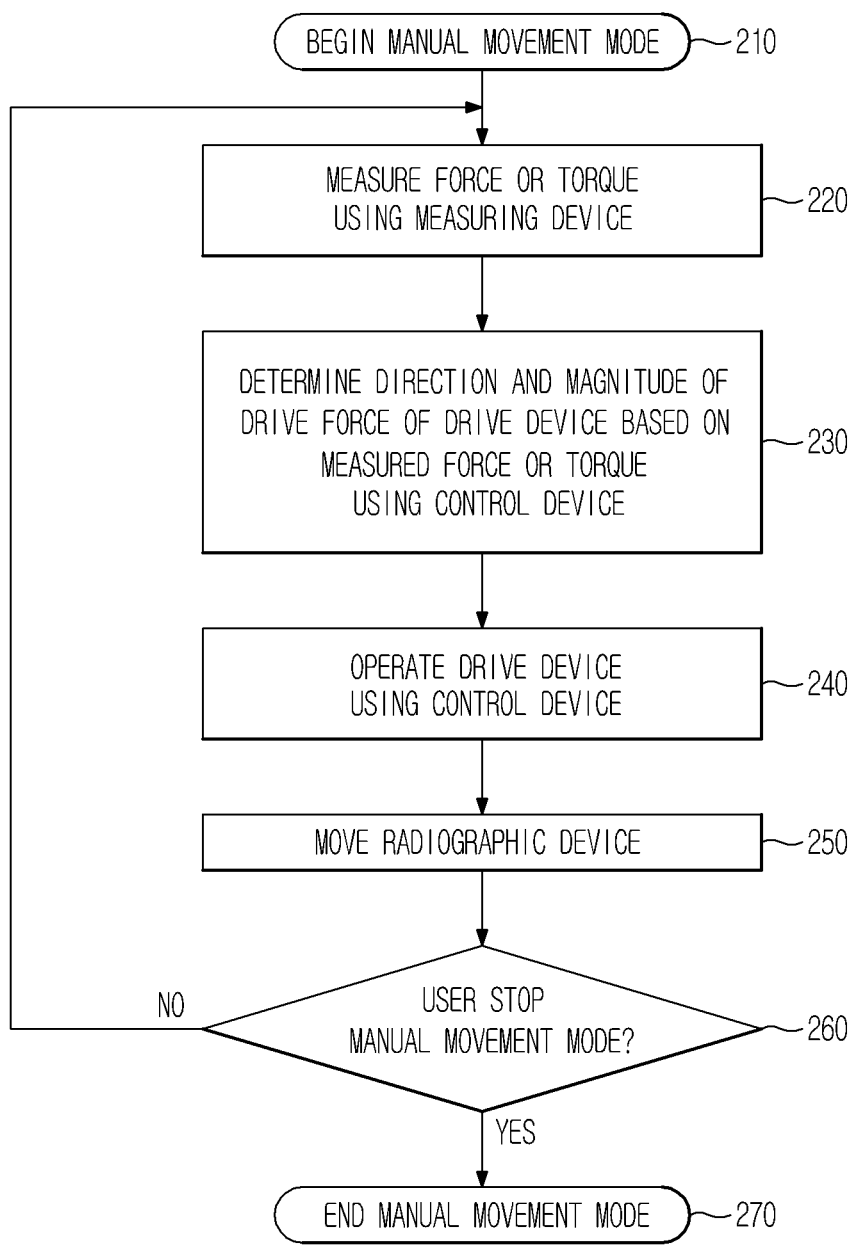
FIG. 6 is a flow chart illustrating a moving method of the radiography system, according to an example embodiment.

FIG. 6 illustrates an example of a moving method of the radiography system.

The user may switch from the automated movement mode to the manual movement mode (210). The user may begin the manual movement mode by operating the mode converter 81 illustrated in FIG. 4. As described above, if the mode converter 81 is integrated with the moving handle 80 illustrated in FIG. 2, the manual movement mode begins in response to the user gripping the moving handle 80.

The measuring device 120 illustrated in FIG. 2 measures force or torque applied to the radiography system (220). The measuring device 120 may transmit a measured value to the control device 130 illustrated in FIG. 2. Alternatively, the control device 130 may monitor the measured force or torque value by periodically receiving electric signals from the measuring device 120.

The control device 130 may determine the direction and magnitude of drive force of the drive device 110 based on the measured force or torque. The direction of drive force of the drive device 110 may coincide with the direction of the measured force or torque and the magnitude of drive force of the drive device 110 may be proportional to the magnitude of the measured force or torque. The proportional relationship between the magnitude of the measured force or torque and the magnitude of drive force of the drive device 100 may be previously input in the control device 130.

The control device 130 may operate the drive device 110 based on the determined direction and magnitude of drive force of the drive device 110 (240). As such, the radiographic device 70 connected to the drive device 110 as illustrated in FIG. 2 may be linearly moved or rotated (250).

A confirmation of whether or not the manual movement mode has ended may be made (260). If the mode converter 81 is integrated with the moving handle 80, the manual movement mode may end when the user releases the moving handle 80 (270). If the manual movement mode does not end, a confirmation of whether or not force or torque is applied to the radiography system 1 may be made (220).

Figure 7:
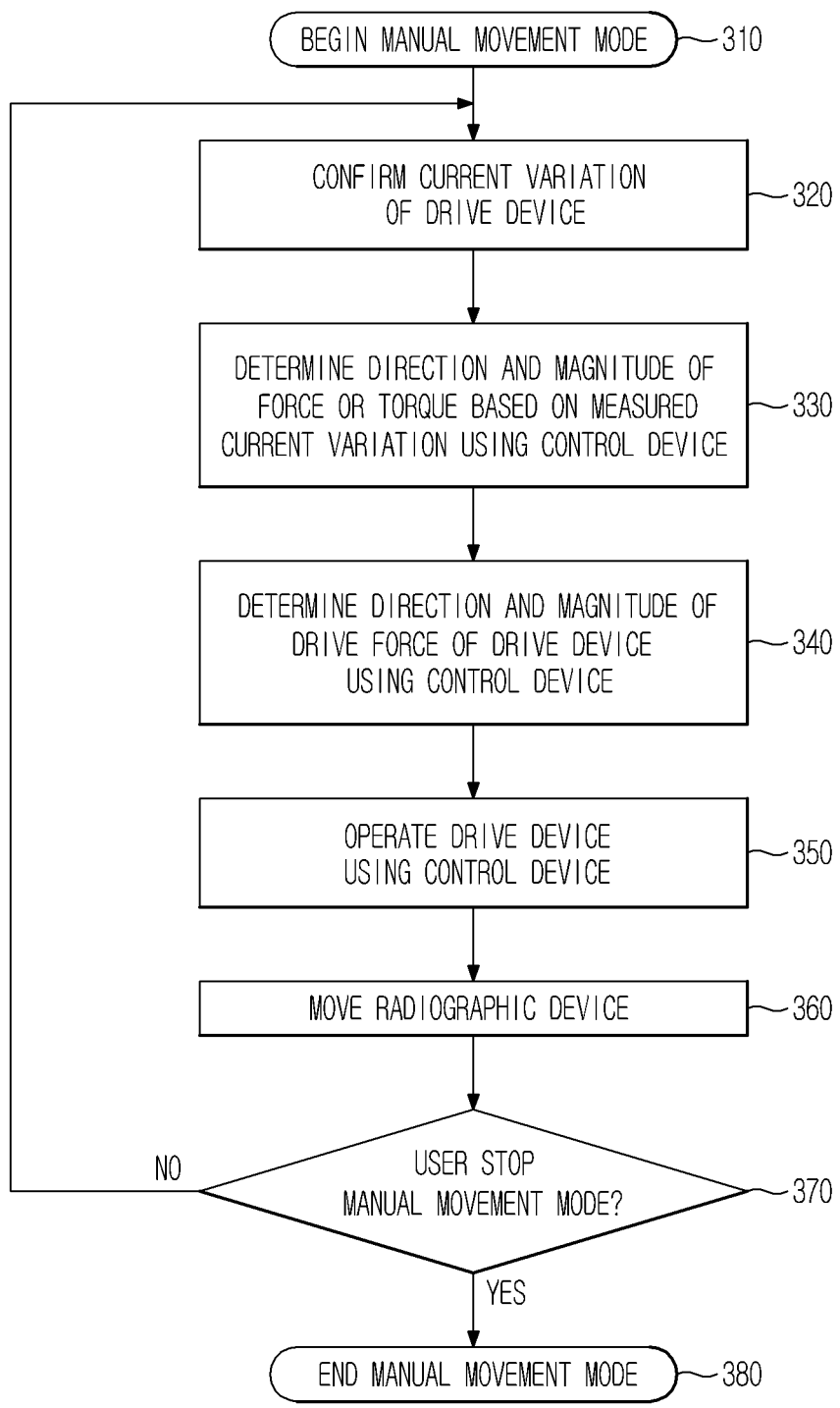
FIG. 7 is a view illustrating the moving method of the radiography system, according to another example embodiment.

FIG. 7 illustrates another example of a moving method of the radiography system.

The drive device 110 illustrated in FIG. 2 may be an electrically driven motor.

If the manual movement mode begins (310), a confirmation of whether or not current flowing through the drive device 110 varies may be made (320). If the user applies force or torque to the radiography system 1 in an idle state of the drive device 110, the force or torque may be transmitted to the drive device 110, causing a variation in the current flowing through the drive device 110. As such, if a measured value of current flowing through the drive device 110 varies, this variation may mean that force or torque is applied to the radiography system 1. In this case, note that the drive device 110 includes the measuring device 120 illustrated in FIG. 1.

The control device 130 illustrated in FIG. 2 may judge the direction and magnitude of force or torque applied to the radiography system 1 based on the measured current variation (330). The current variation measured in the drive device 110 may be proportional to the magnitude of force or torque transmitted to the drive device 110, and the plus or minus sign of the current variation may correspond to the direction of the transmitted force or torque. Thus, if a current value measured when no force or torque is transmitted to the drive device 110 is known, the force or torque applied to the radiography system 1 may be determined using the current variation measured in the drive device 110.

The control device 130 may determine the direction and magnitude of drive force of the drive device 110 based on the previously described direction and magnitude of force or torque applied to the radiography system 1 (340).

The control device 130 may operate the drive device 110 based on the determined direction and magnitude of drive force, and the radiographic device 70 connected to the drive device 110 as illustrated in FIG. 2 may be linearly moved or rotated (360).

A confirmation of whether or not the manual operation mode has ended may be made (370). If the manual operation mode does not end, a confirmation of whether or not current flowing through the drive device 110 varies may be again made.

As is apparent from the above description, in a radiography system according to example embodiments if a user applied force or torque to a radiographic device in an arbitrary direction, a drive device connected to the radiographic device is operated based on the force or torque, which allows the user to easily linearly move or rotate the radiographic device to a desired position. Further, the drive device may be operable even if the user does not directly move the radiographic device in an initial movement stage thereof, which minimizes force or torque that the user has to apply to the radiographic device.

Furthermore, operating the drive device based on force or torque measured by a measuring device may simplify a movement algorithm of the radiographic device, enabling precise linear movement or rotation of the radiographic device.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A radiography system comprising:
a radiographic device configured to be movable;
a handle coupled to the radiographic device; and
a driver configured to selectively move the radiographic device to mimic a motion of an operator of the radiography system, and move the radiographic device in response to the operator inputting an instruction;
wherein the driver is further configured to respond to the operator grasping the handle by switching to a first mode in which the driver moves the radiographic device to mimic the motion of the operator, and respond to the operator releasing the handle by switching to a second mode in which the driver moves the radiographic device in response to the operator inputting the instruction.

2. The radiography system of claim 1, wherein the driver is further configured to move the radiographic device in response to the operator inputting the instruction independent of any motion of the operator.

3. The radiography system of claim 1, wherein the instruction designates a position to which the radiographic device is to be moved by the driver.

4. The radiography system of claim 1, further comprising a measuring device configured to measure a force applied to the radiographic device by the motion of the operator;
wherein the driver is further configured to move the radiographic device to mimic the motion of the operator based on the force measured by the measuring device.

5. The radiography system of claim 4, wherein the measuring device is further configured to measure a magnitude and a direction of the force applied to the radiographic device by the motion of the operator; and
the driver is further configured to move the radiographic device to mimic the motion of the operator based on the magnitude and the direction of the force measured by the measuring device.

6. The radiography system of claim 1, further comprising a supporting structure configured to support the radiographic device so that the radiographic device is movable;
wherein the supporting structure comprises a member configured to be mounted on a surface of a room in which the radiography system is to be used.

7. The radiography system of claim 1, wherein the instruction is an instruction designating a specific movement of the radiographic device.

8. A radiography system comprising:
a radiographic device configured to be movable;
a handle coupled to the radiographic device; and
a driver configured to selectively move the radiographic device by amplifying a physical input, and move the radiographic device in response to inputting of an instruction;
wherein the driver is further configured to respond to the operator grasping the handle by switching to a first mode in which the driver moves the radiographic device by amplifying the physical input, and respond to the operator releasing the handle by switching to a second mode in which the driver moves the radiographic device in response to the inputting of the instruction.

9. The radiography system of claim 8, wherein the driver is further configured to move the radiographic device in response to the inputting of the instruction independent of any physical input.

10. The radiography system of claim 8, wherein the instruction designates a position to which the radiographic device is to be moved by the driver.

11. The radiography system of claim 8, further comprising a measuring device configured to measure a force applied to the radiographic device by the physical input;
wherein the driver is further configured to move the radiographic device by amplifying the physical input based on the force measured by the measuring device.

12. The radiography system of claim 11, wherein the measuring device is further configured to measure a magnitude and a direction of the force applied to the radiographic device by the physical input; and
the driver is further configured to move the radiographic device to move the radiographic device by amplifying the physical input based on the magnitude and the direction of the force measured by the measuring device.

13. The radiography system of claim 8, further comprising a supporting structure configured to support the radiographic device so that the radiographic device is movable;
wherein the supporting structure comprises a member configured to be mounted on a surface of a room in which the radiography system is to be used.

14. The radiography system of claim 8, wherein the instruction is an instruction designating a specific movement of the radiographic device.

15. A radiography system comprising:
a radiographic device configured to be movable;
a handle coupled to the radiographic device; and
a driver configured to selectively move the radiographic device in response to an external force applied to the radiographic device smaller than a force needed to overcome friction of the radiographic device, and move the radiographic device in response to inputting of an instruction;
wherein the driver is further configured to respond to the operator grasping the handle by switching to a first mode in which the driver moves the radiographic device in response to the external force applied to the radiographic device, and respond to the operator releasing the handle by switching to a second mode in which the driver moves the radiographic device in response to the inputting of the instruction.

16. The radiography system of claim 15, wherein the driver is further configured to move the radiographic device in response to the inputting of the instruction independent of any external force applied to the radiographic device.

17. The radiography system of claim 15, wherein the instruction designates a position to which the radiographic device is to be moved by the driver.

18. The radiography system of claim 15, further comprising a measuring device configured to measure the external force applied to the radiographic device;
wherein the driver is further configured to move the radiographic device in response to the external force applied to the radiographic device based on the external force measured by the measuring device.

19. The radiography system of claim 18, wherein the measuring device is further configured to measure a magnitude and a direction of the external force applied to the radiographic device; and
the driver is further configured to move the radiographic device in response to the external force applied to the radiographic device based on the magnitude and the direction of the external force measured by the measuring device.

20. The radiography system of claim 15, further comprising a supporting structure configured to support the radiographic device so that the radiographic device is movable;
wherein the supporting structure comprises a member configured to be mounted on a surface of a room in which the radiography system is to be used.

21. The radiography system of claim 15, wherein the instruction is an instruction designating a specific movement of the radiographic device.

* * * * *